United States Patent [19]

Wendling et al.

[11] 4,262,072
[45] Apr. 14, 1981

[54] POLY(ETHYLENICALLY UNSATURATED ALKOXY) HETEROCYCLIC PROTECTIVE COATINGS

[75] Inventors: Larry A. Wendling; John B. Covington, both of St. Paul, Minn.

[73] Assignee: Minnesota Mining and Manufacturing Company, St. Paul, Minn.

[21] Appl. No.: 51,877

[22] Filed: Jun. 25, 1979

[51] Int. Cl.$^3$ .................... G03G 8/00; B32B 27/06
[52] U.S. Cl. .................... 430/14; 204/159.22; 204/159.23; 204/159.24; 350/398; 351/166; 427/53.1; 427/54.1; 427/162; 427/163; 428/1; 428/411; 428/412; 428/413; 428/457; 428/476.3; 428/424.4; 428/475.8; 428/514; 430/16; 430/18; 430/961; 525/908; 526/262; 526/263; 544/314; 548/312
[58] Field of Search .................... 548/312; 544/314; 204/159.22, 159.23, 159.24, 159.19; 427/54.1, 162, 163, 53; 525/908; 526/262, 263; 428/411, 913, 1, 412, 413, 423, 457, 474, 476, 479; 430/286, 282, 14, 16, 18, 961; 350/155, 166; 352/238; 351/166; 264/2

[56] References Cited

U.S. PATENT DOCUMENTS

| | | | |
|---|---|---|---|
| 3,808,226 | 4/1974 | Habermeier et al. | 548/312 |
| 3,821,098 | 6/1974 | Garratt et al. | 204/159.22 |
| 3,847,769 | 11/1974 | Garratt et al. | 204/159.22 |
| 3,852,302 | 12/1974 | Habermeier et al. | 544/314 X |
| 3,864,358 | 2/1975 | Porret et al. | 544/314 |
| 3,925,349 | 12/1975 | Gaske | 204/159.15 |
| 4,071,477 | 1/1978 | Seltzer et al. | 548/309 X |
| 4,137,139 | 1/1979 | Seltzer et al. | 204/159.23 |

FOREIGN PATENT DOCUMENTS 2734304  2/1978  Fed. Rep. of Germany ........... 548/312

*Primary Examiner*—Ronald H. Smith
*Assistant Examiner*—Thurman K. Page
*Attorney, Agent, or Firm*—Cruzan Alexander; Donald M. Sell; Mark A. Litman

[57] ABSTRACT

Abrasion resistant coatings are comprised of a crosslinked polymeric coating comprising at least 15% by weight of said polymer derived from a polyacrylate material having a heterocyclic nucleus therein.

10 Claims, No Drawings

POLY(ETHYLENICALLY UNSATURATED ALKOXY) HETEROCYCLIC PROTECTIVE COATINGS

FIELD OF THE INVENTION

The present invention relates to novel protective coatings of polyethylenically unsaturated monomers and ethylenically unsaturated crosslinking agents and to coatings comprising only these agents. The invention particularly relates to coatings containing ethylenically unsaturated heterocyclic crosslinking agents.

DESCRIPTION OF THE PRIOR ART

The generation of three dimensional bonding or crosslinking in a composition or coating to reduce the solubility and improve the chemical resistance of a cured product is well known. This is usually effected by the addition of a crosslinking agent to an otherwise two dimensionally polymerizable composition from which the cured product is made. Crosslinking has been produced in products from ethylenically unsaturated compositions such as acrylic compositions (e.g. a methyl methacrylate composition) by incorporation of from about 1 to about 10 percent by weight of a polyacrylic-substituted compound as a crosslinking agent. It is well known that such acrylic compositions generally must be polymerized in an inert, reduced oxygen, atmosphere, e.g., a nitrogen atmosphere. Otherwise, the oxygen present in air will retard or even prevent polymerization of the acrylic composition so that desired levels of polymerization cannot be achieved. At best, only a tacky, incompletely polymerized resin or a weak, low molecular weight polyacrylate resin can be obtained.

Curable, oxygen insensitive acrylic compositions are described in U.S. Pat. Nos. 3,844,916, 3,914,165 and 3,925,349. These references teach that oxygen inhibition can be avoided by incorporation of a Michael adduct of a polyacrylate and an amine having at least one amino hydrogen into acrylic compositions. The use of such an adduct in acrylic photopolymerizable compositions requires the use of a relatively high concentration of polymerization photoinitiator (3% by weight is disclosed at Col. 3, lines 50-51 of U.S. Pat. No. 3,925,349). Although such compositions are useful for coatings and inks that can be cured in the presence of oxygen, these compositions are not satisfactory for coatings that are transparent and where discoloration is undesirable since the use of large amounts of photoinitiator leads to yellowing of the cured coating.

Acrylic compositions, containing 0.5 to 10 percent triphenyl phosphine, that can be cured rapidly in an atmosphere containing 300 to 1000 ppm of oxygen are disclosed in U.S. Pat. No. 4,113,893. Since the provision of atmosphere containing oxygen in any concentration less than that found in air requires use of special equipment, the use of phosphines to obtain rapid curing is also unsatisfactory for many commercial processes.

U.S. Pat. No. 3,968,305 describes acrylic compositions comprising an aliphatic compound having three or more methacryloxy groups that can be polymerized to a crosslinked mar resistant coating. U.S. Pat. No. 4,014,771 teaches that by the addition of (1) 30 to 95 percent of the adduct of methacrylic acid and (2) either a polyglycidyl ether of an aromatic polyhydric compound or a polyglycidyl ester of an aromatic or aliphatic polycarboxylic acid to a polymethacryloyloxy compound such as that described in U.S. Pat. No. 3,968,305, there is obtained a composition which evidently can be polymerized without the necessity of excluding air during the polymerization.

Protective coatings produced by irradiation in the absence of air of the adduct of methacrylic acid to N-glycidylheterocyclic compounds are disclosed in U.S. Pat. Nos. 3,808,226 and 3,847,769.

The compounds of U.S. Pat. No. 3,808,226 bear a similarity in structure to the compounds of the present application. The route of synthesis shown for those compounds cannot produce the compounds of the present invention nor could the route of synthesis used in the present invention produce the compounds of that patent.

Polymerization of the dimethacrylic ester of N-oxyalkylated-heterocyclic compounds is disclosed in U.S. Pat. No. 3,821,098 and 3,852,302.

SUMMARY OF THE INVENTION

In accordance with the invention, there are provided protective coatings consisting essentially of polymerized novel ethylenically unsaturated crosslinking agents comprising poly(ethylenically unsaturated alkoxyalkyl)heterocyclic compounds or comprising copolymerized ethlenically unsaturated monomers and the heterocyclic crosslinking agents of the present invention on a substrate. The crosslinking agents of the invention have the general formula:

$$A^1-Z-A^2 \qquad\qquad I$$

in which $A^1$ and $A^2$ independently are (polyacryloyloxy)alkoxypropyl groups having the general formula:

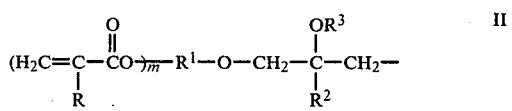

wherein:

R and $R^2$ independently are hydrogen or methyl, m is an integer of 2 to 5, $R^1$ is the residue of an aliphatic polyol group having (m+1) primary hydroxyl groups (said residue being formed by the removal of hydroxyl groups from the polyol) and containing 1 to 10 carbon atoms, preferably one to two quaternary carbon atoms, a valence of m+1, and optionally one catenary oxygen atom, most preferably an alkanol residue, and $R^3$ is preferably hydrogen but can be

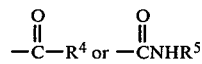

wherein $R^4$ is alkenyl group or alkyl group, preferably alkenyl of 2-5 carbon atoms but can be alkyl having 2 to 5 carbon atoms, $R^4$ of course can be substituted by a phenyl or carboxyl group and $R^5$ is aliphatic or aromatic group having up to 8 carbon atoms and is preferably an acryloyloxyalkyl or a methacryloyloxyalkyl group, Z is a heterocyclic group of the formula:

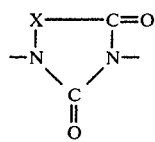

wherein: X is a divalent group which is required to complete a 5- or 6- membered heterocyclic ring. Preferably X is

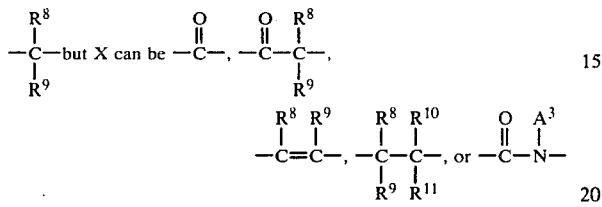

wherein $R^8$, $R^9$, $R^{10}$, and $R^{11}$ are independently hydrogen or lower (1 to 12 carbon atoms) alkyl, preferably methyl, cycloalkyl (3 to 6 carbon atoms) or a phenyl group (preferably up to 16 carbon atoms and most preferably up to 10 carbon atoms) and $A^3$ is as defined above for $A^1$ and $A^3$; in $A^1$, $A^2$ and $A^3$, m is at least 2 and preferably 3.

Excellent diluents for the present invention are represented by Formula I in which $A^1$ and $A^2$ independently are alkoxyalkyl groups having terminal ethylenic unsaturation and having the general formula:

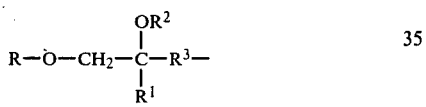

in which R is a monovalent residue of an aliphatic terminally unsaturated primary alcohol, ROH, R having the formula:

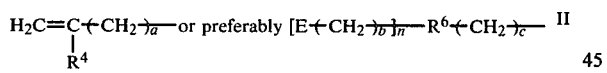

wherein:

E is

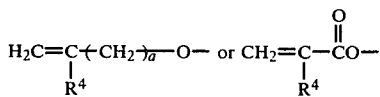

a, c, and d are independently an integer of 1 to 6,
b is zero or an integer of 1 to 6,
$R^1$ and $R^4$ are independently hydrogen or methyl,
$R^6$ is an aliphatic group having 1 to 15 carbon atoms and optionally one or two catenary (i.e., backbone) oxygen atoms, or

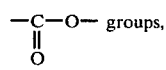

a valence of m+1, and
n is an integer of 1 to 5,
$R^2$ is preferably hydrogen but can be

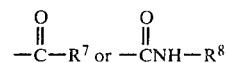

wherein $R^7$ is preferably alkenyl but can be alkyl having 2 to 5 carbon atoms and can be substituted by a phenyl or carboxyl group and $R^8$ is an aliphatic or aromatic group having up to 8 carbon atoms and is preferably an acryloyloxyalkyl or a methacryloyloxyalkyl group,
$R^3$ is an alkylene group having 1 to 6 carbon atoms and optionally one catenary oxygen atom; and
Z is a heterocyclic group of the fomula:

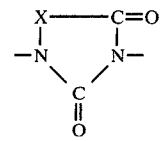

wherein: X is a divalent group which is required to complete a 5- or 6-membered heterocyclic ring, preferably X is

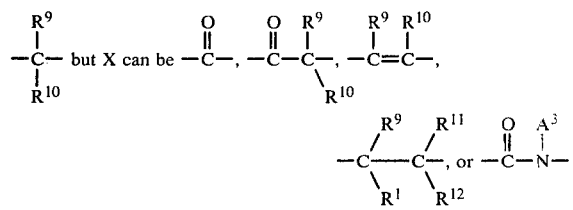

wherein $R^9$, $R^{10}$, $R^{11}$, and $R^{12}$ are independently hydrogen or lower alkyl (of 1 to 12 carbon atoms), cycloalkyl (of 3 to 6 carbon atoms) or phenyl group (of 6 to 12 carbon atoms) and $A^3$ is an alkoxyalkyl group as defined above for $A^1$ and $A^2$.

The preferred diluent compounds used in the invention are those wherein E is

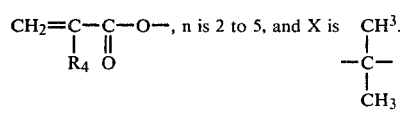

These compounds are preferred because they provide not only a high crosslink density, resulting in improved solvent and abrasion resistance but also excellent adhesion and flexibility. Furthermore, these compounds are water/alcohol soluble and are photocurable to tack free surfaces in the presence of atmospheric oxygen.

DETAILED DESCRIPTION OF THE INVENTION

The compounds used in the coatings of the invention can be prepared by the Lewis acid catalyzed addition of n moles of an ethylenically unsaturated primary alcohol to an epoxy-substituted heterocycle.

Particularly, the (polyacryloyloxy)alkoxypropylheterocyclic compounds used in the coatings of the invention are 5- or 6-membered ring heterocyclic compounds having preferably two (but may have three) nitrogen and preferably two (but may have three) carbonyl groups, viz.

$$\underset{\underset{-C-}{\overset{O,}{\|}}}{}$$

in the ring. At least one but preferably all of the ring nitrogens are substituted by a (polyacrylyoyloxy)alkoxypropyl group (e.g., Formula II). The substituted heterocyclic compounds can be prepared by the Lewis acid catalyzed addition to a heterocyclic compound, as defined, that has one, two or three (where present) of its ring nitrogens substituted by a glycidyl group (e.g., a 2,3-epoxypropyl group) of one, two or three equivalents of a hydroxy compound that is the product of esterification of m hydroxyl groups of a polyol having (m+1) hydroxyl groups with acrylic or methacrylic acid in accordance with the equation:

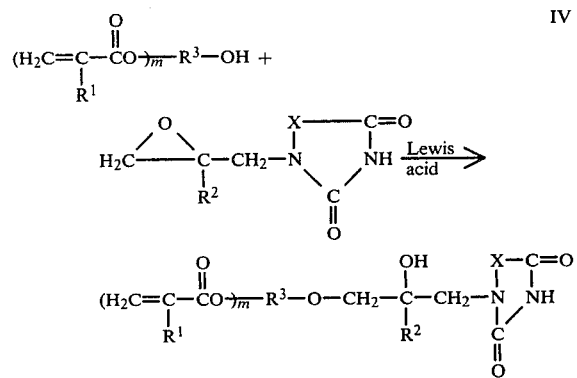

IV wherein $R^1$, $R^2$, m, $R^3$ and X are defined above.

The above equation illustrates the preparation where only one of the ring nitrogens has been substituted by the glycidyl group. Where two or three of the ring nitrogens have been substituted by glycidyl (as is most preferable), two or three equivalents of primary hydroxy compounds can be added. The addition of the hydroxy compound to the glycidyl groups of the heterocyclic compound can be done in one step or in a sequence of steps in whcih first one and then a second and then a third glycidyl group is reacted. It is not necessary that the same hydroxy compound be used in each of the steps. Where two or more different primary hydroxy compounds are used, unsymmetrical compounds are obtained, that is, $A^1$ and $A^2$ (and $A^3$ if three nitrogens on the ring) of Formula I are different. Mixtures of hydroxy compounds can also be used. It is to be expected, however, when two or more hydroxy compounds are used, whether in a sequence of steps or in a one-step mixture, the product obtained will be a mixture of (polyacryloyloxy)alkoxypropylheterocyclic compounds. All, however, are useful in the present invention, particularly when at least about 30% by weight of the polymerizable coating composition is a heterocyclic compound having at least two glycidyl groups reacted with hydroxy compounds in which m in Formula I is at least three, that is, the primary hydroxyl compound to be reacted with the glycidyl group of the heterocyclic compound is preferably a tri- or higher acryloyloxy or methacryloyloxy-alkylhydroxy compound.

The polyglycidyl heterocyclic intermediates useful in the preparation of any and all of the compounds used in the coatings of the present invention are disclosed in U.S. Pat. Nos. 3,808,226 and 4,071,477. Preferably, the reaction is performed in solution. However, it also can be performed in the absence of solvent. Generally, a solution of an epoxy-substituted heterocycle can be added incrementally (over a period of time ranging from a few minutes to several hours) to a mixture of (1) an ethylenically unsaturated primary alcohol (or mixtures of ethylenically unsaturated primary alcohols), (2) an inhibitor for thermal polymerization, and (3) a Lewis acid while maintaining the temperature of the mixture at 50° to 120° C., preferably about 80° to 100° C., until the disappearance of the epoxy group, as indicated by chemical titration or nuclear magnetic resonance spectrometric analysis. Heating the mixture for from 2 to 40 hours usually suffices to complete the reaction, after which volatiles are removed by vacuum distillation.

The compounds of Formula II can then be acylated by reaction with an acylating agent, preferably an acyl halide, an acyl anhydride, or an isocyanate that contains polymerizable ethylenically unsaturated groups.

Exemplary acylating agents include acid chlorides such as acetyl chloride, propionyl chloride, valeryl chloride, dodecanyl chloride, acrylolyl chloride, methacryloyl chloride, alpha-chloroacryloyl chloride, crotyl chloride, benzoyl chloride, phenylacetyl chloride, 2,4-dichlorophenylacetyl chloride; and the corresponding carboxylic acids and anhydrides; other anhydrides include the anhydrides of dicarboxylic acids such as maleic anhydride, succinic anhydride, methylenesuccinic anhydride, phthalic anhydride, and 3-chlorophthalic anhydride; and organic isocyanates such as methyl isocyanate, ethyl isocyanate, n-butyl isocyanate, phenyl isocyanate, 4-t-butyl isocyanate, acryloyloxyethyl isocyanate, methacryloyloxyethyl isocyanate, 4-methacryloyloxybutyl isocyanate, 4-acryloylphenyl isocyanate and 4-vinylphenyl isocyanate.

The compounds of the invention are prepared by addition of a suitable acylating agent to the compound II, e.g. an organic acid anhydride or halide or an organic isocyanate.

Suitable ethylenically unsaturated primary hydroxy compounds for use in the preparation of the compounds of the invention are the hydroxyalkyl acrylates having the formula:

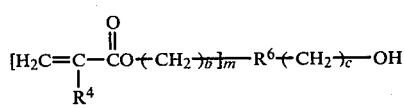

V in which $R^4$, $R^6$, m and c are the same as defined above. Included among suitable hydroxyalkyl acrylates are the monoacrylate and monomethacrylate esters of aliphatic diols such as ethyleneglycol, propyleneglycol, butyleneglycol, hexamethyleneglycol, diethyleneglycol, and dimethylolcyclohexane; the diacrylates and dimethacrylates of aliphatic triols such as trimethylolmethane, 1,1,1-trimethylolpropane, 1,2,3-trimethylolpropane; the triacrylates and trimethacrylates of aliphatic tetrols such as pentaerythritol, 1,1,2,2-tetramethylolethane and 1,1,3,3-tetramethylolpropane; the tetraaacrylates and tetramethacrylates of polyols such as dipentaerythritol and 1,1,1,2,2-pentamethylolethane; and the pentaacrylates and pentamethacrylates of polyols such as tripentaerythritol and hexamethyoloethane.

Other suitable ethylenically unsaturated primary alcohols for use in the preparation of the compounds used in the coatings of the invention are the hydroxyalkenes having the formula:

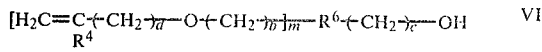

in which $R^4$, $R^6$, m, d, b, and c are the same as defined for compounds of Formula I. Included among suitable hydroxyalkenes are allyl alcohol, methallyl alcohol, allyloxyethyl alcohol, 2-allyloxymethylpropanol (from dimethylolethane), and 2,2-di(allyloxymethyl)butanol (from trimethylolpropane).

Polymerization initiators suitable for use in the crosslinkable compositions producing coatings of the invention are compounds which liberate or generate a free-radical on addition of energy. Such initiators include peroxy, azo, and redox systems each of which are well known and are described frequently in polymerization art, e.g. Chapter II of *Photochemistry*, by Calvert and Pitts, John Wiley & Sons (1966). Included among free-radical initiators are the conventional heat activated initiators such as organic peroxides and organic hydroperoxides; examples are benzoyl peroxide, tertiary-butyl perbenzoate, cumene hydroperoxide, azobis(isobutyronitrile) and the like. The preferred initiators are photopolymerization initiators which facilitate polymerization when the composition is irradiated. Included among such initiators are acyloin and derivatives thereof, such as benzoin, benzoin methyl ether, benzoin ethyl ether, benzoin isopropyl ether, benzoin isobutyl ether, and α-methylbenzoin; diketones such as benzil and diacetyl, etc.; organic sulfides such as dihenyl monosulfide, diphenyl disulfide, decyl phenyl sulfide, and tetramethylthiuram monosulfide; S-acyldithiocarbamates, such as S-benzoyl-N,N-dimethyldithiocarbamate; phenones such as acetophenone,α,α,α-tribromoacetophenone, α,α-diethoxyacetophenone, 2,2-dimethoxy-2-phenylacetophenone, O-nitro-α,α,α-tribromoacetophenone benzophenone, and p,p'-tetramethylciaminobenzophenone; aromatic iodonium and aromatic sulfonium salts; sulfonyl halides such as p-toluenesulfonyl chloride, 1-naphthalenesulfonyl chloride, 2-naphthalenesulfonyl -chloride, 1,3-benzenedisulfonyl chloride, 2,4-dinitrobenzenesulfonyl bromide and p-acetamidobenzenesulfonyl chloride. Normally the initiator is used in amounts ranging from about 0.01 to 5% by weight of the total polymerizable composition. When the quantity is less than 0.01% by weight, the polymerization rate becomes extremely low. If the initiator is used in excess of 5% by weight, no correspondingly improved effect can be expected. Thus, addition of such greater quantity is economically unjustified. Preferably, about 0.25 to 1.0% of initiator is used in the polymerizable compositions.

The crosslinkable compositions of the invention are preferably diluted with up to 85% by weight of any ethylenically unsaturated monomer. Preferably the majority of comonomers are at least diethylenically unsaturated monomers. Generic classes include the acrylates, methacrylates, acrylic anhydrides, ethylenically unsaturated anhydrides, olefinic compounds, acrylamides, ethylenically unsaturated aminos and urethanes, vinyl esters, vinyl ethers, vinyl halides, vinyl epoxy resins, vinyl silanes and siloxanes, vinyl heterocycles, and prepolymers and polymers of these materials. Particularly suitable ethylenically unsaturated monomers include methyl methacrylate, ethyl acrylate, 2-ethylhexyl acrylate, cyclohexyl acrylate, styrene, butadiene, 2-chlorostyrene, 2,4-dichlorostyrene, acrylic acid, acrylamide, acrylonitrile, t-butyl acrylate, methyl acrylate, butyl acrylate, N-vinyl pyrrolidone, 2-(N-butylcarbomyl)ethyl methacrylate and 2-(N-butylcarbamyl)ethyl methacrylate and 2-(N-ethylcarbamyl) ethyl methacrylate. Preferably 35 to 80% and most preferably 45 to 60% by weight of copolymerizable components comprise the heterocyclic agents of the present invention. Other diluting monomers that can be incorporated into the composition of the invention include 1,4-butylene dimethacrylate or acrylate, ethylene dimethacrylate, hexamethylene diacrylate or dimethacrylate, glycerol diacrylate or methacrylate, glycerol triacrylate or trimethacrylate, pentaerythritol triacrylate or trimethacrylate, pentaerythritol tetraacrylate or tetramethacrylate, diallyl phthalate, dipentaerythritol pentaacrylate, neopentylglycol triacrylate, and 1,3,5-tri(2-methacryloxyethyl)-s-triazine.

The crosslinkable composition used in preparing coatings can also contain a viscosity modifier or binder. Generally, up to about 50 percent by weight of a compatible polymer is used. Preferably, the polymer is an acrylic polymer such as poly(acrylic acid), a poly(methacrylic acid), poly(methyl methacrylate), poly(vinyl chloride), poly(vinyl acetate, poly(vinyl butyral) and the like. Other polymers include polyethers, polyesters, polylactones, polyamides, polyurethanes, cellulose derivatives, polysiloxanes and the like.

The compositions used in preparing coatings of the invention can also include a variety of addenda utilized for their known purpose, such as stabilizers, inhibitors, lubricants, flexibilizers, pigments, carbon black, dyes, reinforcing fillers such as finely divided silica, non-reinforcing fillers such as diatomaceous earth, metal oxides, asbestos, fiberglass, glass bubbles, talc, etc. Fillers can generally be used in proportions up to about 200 percent by weight of the curable components but preferably are used up to about 50 percent by weight. Where the polymerizing energy is radiation, it is desirable that the addenda be transparent to the radiation.

The compositions used in preparing coatings of the invention are prepared by simply mixing (under "safe light" conditions if the composition is to be sensitized to visible light) the polymerization initiator and sensitizer (where used), the poly(ethylenically unsaturated alkoxyalkyl)heterocyclic compound, diluting monomers, binders and addenda. Inert solvents may be employed if desired when effecting this mixture. Examples of suitable solvents are methanol, ethanol, acetone, acetonitrile and includes any solvent which does not react with the components of the mixture.

The compositions may be applied to the substrates before curing in any conventional fashion. Roller coating, spray coating, knife-edge coating, dip-coating, sputter coating, bar coating and any other conventional process for the application of liquids to substrates may be used.

Substrates

The coatings of the present invention find application useful on substantially any solid substrate. Because the coatings of the present invention can be cured by radication, even highly temperature sensitive substrates can be coated. The substrates may be in substantially any form, such as sheets, films, fibers, fabrics and shaped solid objects. Amongst the substrates particularly finding advantages with coatings of the present invention are polymeric resins, including both thermoplastic and thermoset resins (e.g., polyesters, polyethers, polyamides, polyurethanes, polycarbonates, polyacrylates, polyolefins, polyvinyls, cellulose esters, epxoy resins, polysiloxanes, etc.), ceramic substrates, including glass, fused ceramic sheeting, and fibers, metals and metallized surfaces, natural cellulosic materials, including wood and paper, natural resins, including rubber and gelatin and other various solid surfaces. The coatings are useful particularly on refractive substrates (e.g., lenses, prisms and the like) as well as reflective substrates (street signs, mirrors, etc.). They are also useful on metallized polymeric film which is transparent and used as a light screen on windows.

Where the coating compositions of this invention are not naturally adherent to the particular substrate selected, primer compositions, comprising single ingredients or blends of materials, may be used to improve the bond of the coating to the substrate. Texturizing, chemical, or physical treatment of the surface may also be used to improve bonding. The coatings of the invention are generally between 0.5 and 500 microns thick, preferably between 1 and 50 microns, and most preferably between 3 and 25 microns.

Particularly useful substrates for application of the coatings of the present invention would be those requiring transparent protective coatings. Finished photographic prints and films, paintings, transparencies, car windshields, painted surfaces, instant film (i.e., film which does not require external application of developing chemistry), photothermographic and thermographic paper and film, photoconductive substrates, opthalmic lenses, liquid crystal displays, motion picture film, street and traffic signs, reflective surfaces, retroreflective surfaces, traffic lights, and many other substrates are usefully coated according to the practice of the present invention. These coatings are particularly useful on optionally functional surfaces or elements, particularly polarizing elements. These include both polymeric film type polarizers and the solvent—coated type polarizers such as are described in U.S. Pat. Nos. 2,400,877; 2,481,830; and 2,544,659.

Where the polymerization initiator is a photoinitiator, the composition can be a composition for in situ curing because of this insensitivity to oxygen.

The photopolymerizable compositions are particularly suitable for applications in the field of protective coatings and graphic arts because of their superior abrasion-resistance and adhesion to many rigid, resilient and flexible substrates such as metals, metal oxides, plastics, rubber, glass, paper, wood, and ceramics; their excellent resistance to most solvents and chemicals; their excellent flexibility and weatherability; and their capability for forming high resolution images.

Curing

The photopolymerization of the compositions of the invention occurs on exposure of the compositions to any source of radiation emitting actinic radiation at a wavelength within the ultraviolet and visible spectral regions. Suitable sources of radiation include mercury, xenon, carbon arc and tungsten filament lamps, sunlight, etc. Examples may be from less than about 1 second to 10 minutes or more depending upon the amounts of the particular polymerizable materials and photopolymerization catalyst being utilized and depending upon the radiation source, distance from the souce, and the thickness of the coating to be cured. The compositions may also be polymerized by exposure to electron beam irradiation. Generally speaking, the dosage necessary is from less than 1 megarad to 100 megarad or more. One of the major advantages with using electron beam curing is that highly pigmented compositions can be effectively cured at a faster rate than by mere exposure to actinic radiation.

These and other features of the present invention will be known in the following Examples.

EXAMPLE 1

Preparation of
1,3-Bis(3-[2,2,2-(triacryloyloxymethyl)ethoxy 2-hydroxypropyl]-5,5-dimethyl-2,4-imidizolidinedione

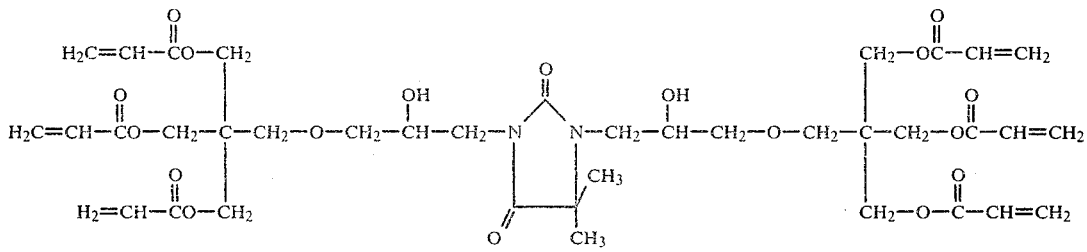

Compound A

Pentacerythritol triacrylate (44.3 g, 0.1 m, hydroxyl equivalent weight of 443), 0.025 g 4-methoxyphenol, and 0.4 g borontrifluoride etherate were charged into a 250 ml three- and necked round bottom flask equipped with mechanical stirrer, pressure equalizing dropping funnel, reflux condenser, and a $CaCO_4$ drying tubel. (It is to be noted that most commercially available pentaerythritol triacrylate is contaminated with acrylated impurities.) The reaction flask was heated to 60° C. and 13.8 g of 1,3-bis(2,3-epoxypropyl)-5,5-dimethyl-2,4-imidizolidinedione (0.1 m peroxide equivalency) in 5 ml chloroform was added dropwise over 45 minutes. After the addition, the reaction flask temperature was raised to 85° C. and stirred for 11.5 hours. After this time, titration of an aliquote for unreacted epoxide indicated that the reaction was greater than 99% complete. The chloroform was removed by vacuum distillation leaving as residue a viscous liquid that contains predominently compounds of the structure of Compound A. Photocurable impurities introduced with the pentaerythritol triacrylate can be removed by trituration with diethyl ether.

A mixture of the liquid and 2% by weight of the photopolymerization initiator 2,2-dimethoxy-2-phenylacetophenone was coated onto 12μm polyester film and dried to provide a 2.5μm layer. The layer was then cured in a UV Processor, Model No. CC 1202 N/A (manufactured by Radiation Polymer Co.) after one pass at 12 m/min. (40 feet/min.) under an 80 watts/cm (200 watts/inch) medium pressure mercury lamp. The cured layer exhibited 95–100% cross-hatch adhesion, 2–7% Taber Haze, 13–16% haze in the Gardner Falling Sand Abrader (i.e., tested according to ASTM Designation D1003-64(Procedure A) and excellent resistance to abrasion be steel wool. The layer was unaffected by treatment with ethanol, acetone, ethyl acetate, toluene, hexane, aqueous sodium hydroxide and 10% aqueous hydrochloric acid.

EXAMPLE 2 the cure time is reduced to 80 seconds and with increasing amounts of A, the composition cures faster until at 100% A, the composition under the stated conditions cures in only 10 seconds. Comparable results can be obtained with Compound B.

EXAMPLE 9

Preparation of 1,3-Bis[3-(2-allyloxyethoxy)-2-hydroxypropyl]-5,5-dimethyl-2,4-imidizolidinedione

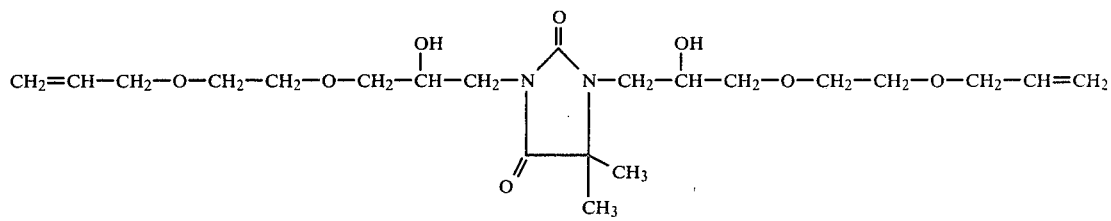

Preparation of 1,3Bis[3-(2-acryloyloxyethoxy)-2-hydroxypropyl]-5,5-dimethyl-2,4-imidizolidinedione

Compound B

Distilled hydroxyethyl acrylate (46.4 g, 0.4 m), 0.065 g 4-methoxyphenyl, and 1.0 g borontrifluoride etherate were charged into a 250 ml three-necked round bottom flask equipped with mechanical stirrer, pressure equalizing dropping funnel, reflux condenser, and $CaCO_4$ drying tube. The reaction flask was heated to 60° C. and 55.2 g 1,3-bis-(2,3-epoxypropyl)-5,5-dimethyl-2,4-imidizolidenedione in 10 ml chloroform was added dropwise over 30 minutes. The reaction flask temperature was raised to 75° C. for 11 hours. At this time titration of residual epoxide groups indicated that the reaction was 97% complete. The volatiles were removed by vacuum distillation leaving as residue a colorless liquid.

A layer of the compound containing 2% of 2,2-dimethoxy-2-phenylacetophenone was prepared and cured as in Example 1. The cured layer had chemical resistance similar to that of the layer of Example 1.

EXAMPLES 3–8

Various amounts of Compounds A and B were mixed with trimethylolpropanetriacrylate (TMPTA) and 2% by weight of the photopolymerization initiator of Example 1 added. Each mixture was diluted with an equal weight of acetone and coated onto 12μ m polyester film and dried. The dried coating was 2.5μm thick. On exposure in air at a distance of 6 cm the radiation from a 100 watt Hanovia 3D690 lamp and the time measured at which each become insoluble in acetone. The data obtained is recorded in Table I.

TABLE I

| Exp. No. | Composition | | Cure Time (Sec.) |
|---|---|---|---|
| | Compound (%) | TMPTA | |
| 3 | None | 100 | 600 |
| 4 | A (17) | 83 | 80 |
| 5 | A (28) | 72 | 60 |
| 6 | A (50) | 50 | 50 |
| 7 | A (100) | 0 | 10 |
| 8 | B (100) | 0 | 30 |

By reference to TAble I it can be seen that TMPTA requires 10 minutes to reach insolubility and that with the addition of 17% of Compound A (from Example 1)

Compound F 2-allyloxyethanol (20.43 g, 0.1 m), 0.03 g 4-methoxyphenol, and 0.30 g boron-trifluoride etherate were charged into a 250 ml three-necked round bottom flask equipped with mechanical stirrer, pressure equalizing dropping funnel, reflux condenser and $CaSO_4$ drying tube. The reaction flask temperature was heated to 80° C. and 13.8 g 1,3-diglycidyl-5,5-dimethyl hydantoin in 4.5 g chloroform was added dropwise over 30 minutes. The reaction was maintained at 80° for 17 hours. At this time titration of residual epoxide groups indicated that the reaction was 99% complete. The chloroform was removed by vacuum distillation leaving as residue a viscous liquid.

EXAMPLE 9

Into a 250 ml three-necked round bottom flask equipped with mechanical stirrer, pressure equalizing dropping funnel, reflux condenser, and calcium sulfate drying tube were charged 103.0 g pentaerythritol triacrylate (hydroxy equivalent weight of 515), 23.2 g 2-hydroxyethyl acrylate (0.2 m), 0.08 g 4-methoxyphenol, and 1.0 g boron-trifluoride etherate. The reaction flask was heated to 75° C. and 55.2 g (0.40 m epoxy equivalency) 1,3-bis(2,3-epoxypropyl)-5,5-dimethyl-2,4-imidizolidinedione in 20 ml chloroform was added dropwise over one hour. After the addition, the reaction flask temperature was raised to 88° C. and stirred for 18.0 hours. At this time, titration of an aliquote for unreacted epoxide indicated the reaction was greater than 99% complete. The volatiles were removed by vacuum distillation leaving a viscous liquid which contains a mixture of bis(triacrylolyl)-, bis(monoacryloyl)-, and the unsymmetrical monoacrylolyl-triacryloyl-imidizolidinedione, and impurities, introduced with the pentaerythritol triacrylate.

A layer of the reaction product of Example 15, prepared to contain 2% Irgacure 651 and cured as described in Example 1, had abrasion and chemical resistance characteristics similar to those of the layer of Example 1.

EXAMPLES 10–17

Coatings about 10 micrometers thick were prepared by coating using a Meyer bar onto about 12 m polyethylene film primed with polyvinylidene chloride, a 50% solution in ethyl acetate (other solvents such as ketones and lower alcohols are equally suitable), and drying mixtures of the product of Example 1 (a mixture of Compound A and pentaerythritol tetraacrylate that is designated A and PTA, respectively, in Table I) and zero to 100% of Compound B (from Example 2) based on total weight of Compound A, T and B. To each solution had been added, as photoinitiator, 1% of Irgacure 651, the acetophenone of Example 2, (similar results were obtained with α,α-diethoxyacetophenone and benzoin ethyl ether and, as coating aid, 0.01% of a fluorocarbon or silcone surfactant. The dried coatings were then cured by one pass in a Model 1202 AN(PPG) Ultraviolet Processor (manufactured by Radiation Polymer Company) operated at about ½ m/min with an 80 watt/m medium pressure mercury vapor lamp 15 cm from the surface of the layer without exclusion of air. The cured layer was tested for cross-hatch adhesion, Taber wheel abrasion, resistance to steel wood, and falling sand abrasion. The results are recorded in Table I.

TABLE I

| Ex. No. | Composition | | | Cross-Hatch Adhesion % | Abrasion Resistance | | |
|---|---|---|---|---|---|---|---|
| | % A | % PTA | % B | | Taber % Haze | Falling Sand % Haze | Steel wool |
| 3 | 75 | 25 | 0 | 100 | 2–7 | 13–16 | Excellent |
| 4 | 67.5 | 22.5 | 10 | 100 | 2–7 | 13–16 | Excellent |
| 5 | 60 | 20 | 20 | 100 | 2–7 | 13–16 | Excellent |
| 6 | 52.5 | 17.5 | 30 | 100 | 5–9 | | Excellent |
| 7 | 45 | 15 | 40 | 100 | 5–9 | | Excellent |
| 8 | 37.5 | 12.5 | 50 | 100 | 5–9 | | Excellent |
| 9 | 30 | 10 | 60 | 100 | 28–34 | | Fair |
| 10 | 0 | 0 | 100 | | | | |

Table I shows that coatings prepared form the hexaacrylolyoxyhydantoin, Compound A, and up to more than 50% of the diacryloyloxyhydantoin, Compound B, have excellent resistance to abrasion as measured by Taber, falling sand and steel wool procedures. At up to about 30% Compund B, abrasion resistance is superior, but continues to be acceptable to a limit of about 15%.

When coatings were prepared as for Examples 3–10 but using photoinitiator concentrations from 0.4 to 3% and tested, similar abrasion resistance and cross-hatch adhesion was obtained. For comparison, coatings prepared by coating a substrate with α-glycidoxypropyl-trimethoxysilane containing 1% diphenyliodonium hexafluoroantimonate and exposing to ultraviolet until cured had a Taber abrasion of 5 to 9 and an abrasion resistance of 15 to 20 by the falling sand method.

EXAMPLES 18–28

Example 3 was repeated using the substrates listed in Table II in place of primed polyester. The abrasion resistance and adhesion obtained for each is given in Table II.

TABLE II

| Ex. No. | Substrate | Cross-Hatch Adhesion % | Abrasion Resistance | | |
|---|---|---|---|---|---|
| | | | Taber % Haze | Falling Sand % Haze | Steel wool |
| 11 | Polyester | 95–100 | 2–7 | 13–16 | Excellent |
| 12 | Primed Polyester | 100 | 2–6 | 13–16 | Excellent |
| 13 | Polyethylene | 95–100 | 2–7 | 13–16 | Excellent |
| 14 | Polyvinylchloride | 95–100 | 2–7 | 13–16 | Excellent |
| 15 | Polycarbonate[1] | 95–100 | 2–7 | 13–16 | Excellent |
| 16 | Polymethyl methacrylate | 90–100 | 2–7 | 13–16 | Excellent |
| 17 | Polyurethane | 90–95 | 2–7 | 13–16 | Excellent |
| 18 | Epoxy[2] | 95–100 | 2–7 | 13–16 | Excellent |
| 19 | Cellulose triacetate | 95–100 | 2–7 | 13–16 | Excellent |
| 20 | Cellulose diacetate | 95–100 | 2–7 | 13–16 | Excellent |
| 21 | Glass | | 2–7 | 13–16 | Excellent |

[1]Lexan ® trade name for General Electric's polycarbonate
[2]Polymer obtained by polymerization of diglycidyl ether of Bisphenol A using 0.25% SbF$_5$

We claim:

1. A coated substrate comprising a substrate having adhered on at least one surface thereof a crosslinked polymeric coating having at least 15% by weight of the polymeric coating derived from a poly(ethylenically unsaturated alkoxyalkyl)heterocyclic compound of the formula:

$$A^1-Z-A^2$$

wherein $A^1$ and $A^2$ are independently groups having the formula $$(CH_2=C-\underset{R}{C}-O)_m-R^1-O-CH_2-\underset{R^2}{\overset{OR^3}{C}}-CH_2-$$

wherein
R and $R^2$ are independently hydrogen or methyl,
$R^1$ is the residue of an aliphatic polyol group having m+1 primary hydroxyl groups and 1 to 10 carbon atoms, said residue being formed by the removal of hydroxyl groups from the polyol, and having a valence of m+1,
$R^3$ is selected from hydrogen, $$-\overset{O}{\underset{\|}{C}}-R^4, \text{ and } -\overset{O}{\underset{\|}{C}}NHR^5$$

wherein $R^4$ is an alkenyl or alkyl group, and $R^5$ is an aliphatic or aromatic group of up to 8 carbon atoms,
m is an integer of 2 to 5, and
Z is a heterocyclic group of the formula

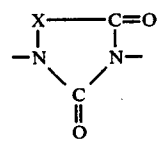

wherein X is a divalent group which is required to complete a 5- or 6-membered heterocyclic ring.

2. The coated substrate of claim 1 wherein X is selected from the group consisting of

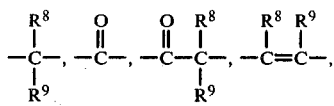

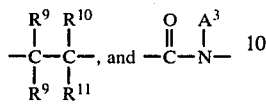

wherein $R^8$, $R^9$, and $R^{11}$ are independently selected from the group of hydrogen, alkyl group of 1 to 12 carbon atoms, cycloalkyl group of 3 to 6 carbon atoms, or phenyl group, and $A^3$ is independently

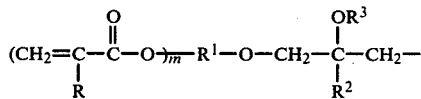

wherein R, $R^1$, $R^2$, $R^3$ and m are as defined above.

3. The coated substrate of claim 2 wherein X is

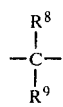

and $R^8$ and $R^9$ are selected from hydrogen and alkyl of 1 to 5 carbon atoms.

4. The coated article of claim 3 in which m is 3.

5. The coating on a substrate of claim 1 in which from 35 to 80% by weight of said polymeric coating is derived from said heterocyclic compound.

6. The coating on a substrate of claim 5 wherein said substrate is an organic oligomeric resin.

7. The coating on a substrate of claim 5 wherein said substrate is selected from the group consisting of photographic film and motion picture film.

8. The coating on a substrate of claim 5 wherein said substrate is a refractive or reflective substrate.

9. The coating on a substrate of claim 5 wherein said substrate is a transparent metallized polymer film.

10. The coating on a substrate of claim 5 wherein said substrate is a polarizing element.

* * * * *

UNITED STATES PATENT AND TRADEMARK OFFICE
CERTIFICATE OF CORRECTION

PATENT NO. : 4,262,072

DATED : April 14, 1981

INVENTOR(S) : Larry A. Wendling & John B. Covington

It is certified that error appears in the above—identified patent and that said Letters Patent is hereby corrected as shown below:

Col. 8, line 1, delete "(N-butylcarbomyl-" and replace with --(N-butylcarbamyl- --.

Col. 8, lines 10 and 11, in both instances delete "glycerol" and replace with --gylceryl--.

Col. 10, line 8, delete "souce" and replace with --source--.

Col. 10, line 44, delete "tubel" and replace with --tube--.

Col. 11, line 29, delete "$CaCO_4$" and replace with --$CaSO_4$--.

Col. 13, line 16, delete "1/2" and replace with --12--.

Col. 13, line 17, delete "watt/m" and replace with --watt/cm--.

Col. 13, line 20, delete "wood" and replace with --wool--.

Col. 13, line 49, delete "α-glycidoxypropyl-" and replace with --γ-glycidoxypropyl- --.

Signed and Sealed this

Eighth Day of December 1981

[SEAL]

Attest:

Attesting Officer

GERALD J. MOSSINGHOFF

Commissioner of Patents and Trademarks